United States Patent
Morita et al.

(10) Patent No.: US 12,246,118 B2
(45) Date of Patent: Mar. 11, 2025

(54) ATTACHING MEMBER

(71) Applicant: Nikkiso Company Limited, Tokyo (JP)

(72) Inventors: Masayuki Morita, Shizuoka (JP); Kazuhide Ono, Shizuoka (JP)

(73) Assignee: Nikkiso Company Limited, Tokyo (JP)

( * ) Notice: Subject to any disclaimer, the term of this patent is extended or adjusted under 35 U.S.C. 154(b) by 681 days.

(21) Appl. No.: 17/350,408

(22) Filed: Jun. 17, 2021

(65) Prior Publication Data
US 2021/0316057 A1 Oct. 14, 2021

Related U.S. Application Data

(63) Continuation of application No. PCT/JP2019/051338, filed on Dec. 26, 2019.

(30) Foreign Application Priority Data

Dec. 27, 2018 (JP) .................................. 2018-246175

(51) Int. Cl.
| | | |
|---|---|---|
| A61M 1/14 | (2006.01) | |
| A61M 1/34 | (2006.01) | |
| A61M 1/36 | (2006.01) | |
| A61M 60/113 | (2021.01) | |
| A61M 60/279 | (2021.01) | |
| A61M 60/37 | (2021.01) | |

(52) U.S. Cl.
CPC ............ *A61M 1/14* (2013.01); *A61M 1/3424* (2014.02); *A61M 1/367* (2013.01); *A61M 60/113* (2021.01); *A61M 60/279* (2021.01); *A61M 60/37* (2021.01)

(58) Field of Classification Search
CPC ........ A61M 1/16; A61M 1/34; A61M 1/3649; A61M 1/36
See application file for complete search history.

(56) References Cited

U.S. PATENT DOCUMENTS

| | | | |
|---|---|---|---|
| 4,079,007 A * | 3/1978 | Hutchisson | A61M 1/1605 210/321.71 |
| 2014/0012202 A1* | 1/2014 | Schaefer | F04B 43/1253 604/151 |
| 2014/0219829 A1* | 8/2014 | Matsuo | A61M 60/857 417/63 |

FOREIGN PATENT DOCUMENTS

| | | |
|---|---|---|
| EP | 2682608 A1 | 1/2014 |
| JP | S60-148069 U | 10/1985 |

(Continued)

OTHER PUBLICATIONS

JP06292722A—Translation (Year: 1994).*

(Continued)

*Primary Examiner* — Walter D. Griffin
*Assistant Examiner* — Cameron J Allen
(74) *Attorney, Agent, or Firm* — Young Basile Hanlon & MacFarlane, P.C.

(57) ABSTRACT

An attaching member attachable to a blood purification apparatus including a peristaltic pump, the attaching member holding a pump tube to be squeezed in a predetermined direction by the peristaltic pump for liquid delivery. The attaching member includes a body attachable to a predetermined position of the blood purification apparatus, and a holding portion attached to the body and that holds the pump tube. The holding portion holds the pump tube such that the pump tube is inclined in a direction in which the pump tube is attached to the peristaltic pump.

20 Claims, 15 Drawing Sheets

(56) References Cited

FOREIGN PATENT DOCUMENTS

| | | | |
|---|---|---|---|
| JP | 06292722 A | * | 10/1994 |
| JP | 2005-074234 A | | 3/2005 |
| JP | 2006-212050 A | | 8/2006 |
| JP | 2008-000425 A | | 1/2008 |
| JP | 2010-190062 A | | 9/2010 |
| JP | 2015-073847 A | | 4/2015 |
| JP | 2015-202248 A | | 11/2015 |
| JP | 2017-140521 A | | 8/2017 |
| JP | 2017-164285 A | | 9/2017 |
| WO | 1995/017603 A1 | | 6/1995 |
| WO | 1996/040322 A2 | | 12/1996 |
| WO | 2013/090579 A1 | | 6/2013 |
| WO | 2013/098028 A1 | | 7/2013 |
| WO | 2018/225027 A1 | | 12/2018 |

OTHER PUBLICATIONS

Potentially related to U.S. Appl. No. 17/347,852, filed Jun. 15, 2021, and previsouly published as WO2020/137016 A1.
Potentially related to U.S. Appl. No. 17/348,037, filed Jun. 15, 2021, and previously published as WO2020/138380 A1.
Potentially related to U.S. Appl. No. 17/348,051, filed Jun. 15, 2021, and previsouly published as WO2020/138381 A1.
Potentially related patent application that will be filed with the USPTO, and is published as WO2020/138384 A1.
Potentially related patent application that will be filed with the USPTO, and is published as WO2020/138383 A1.

* cited by examiner

[Fig. 1]
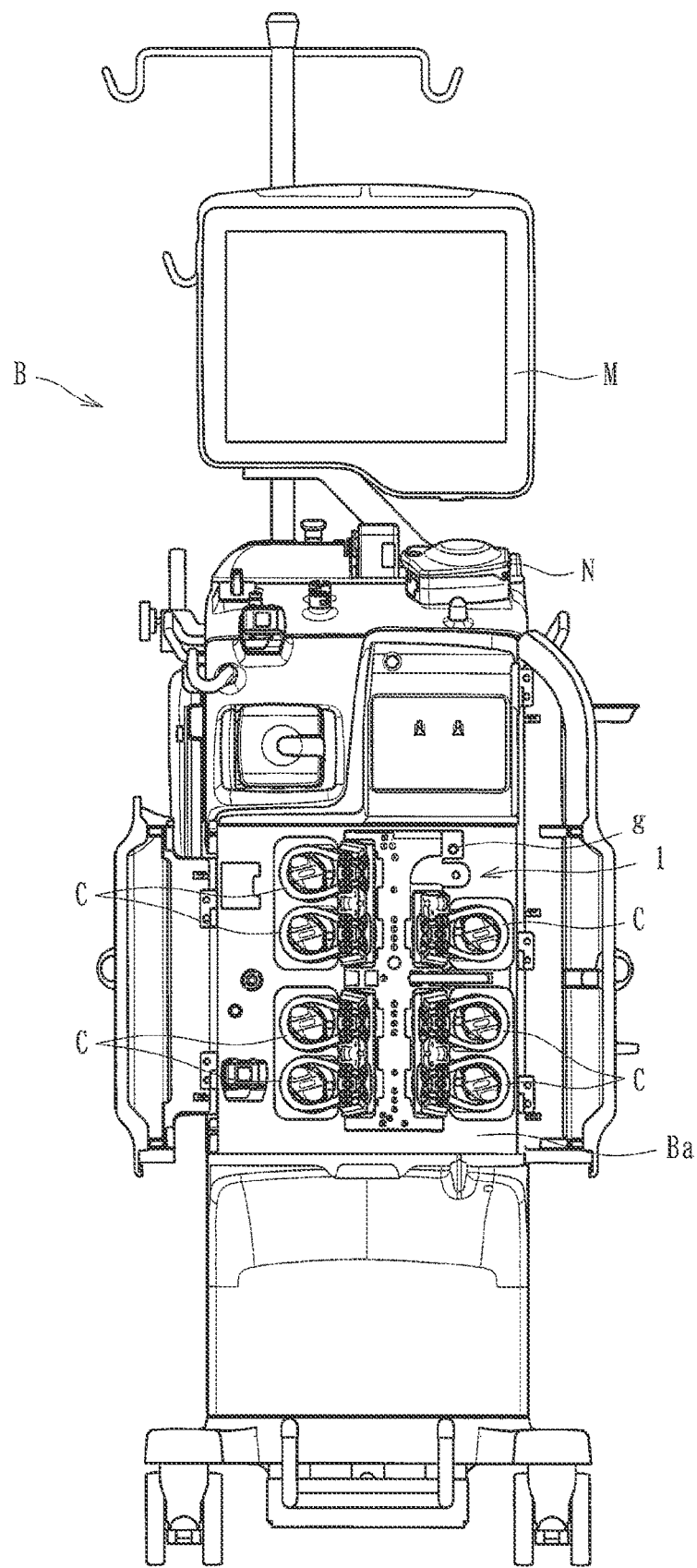

[Fig. 2]
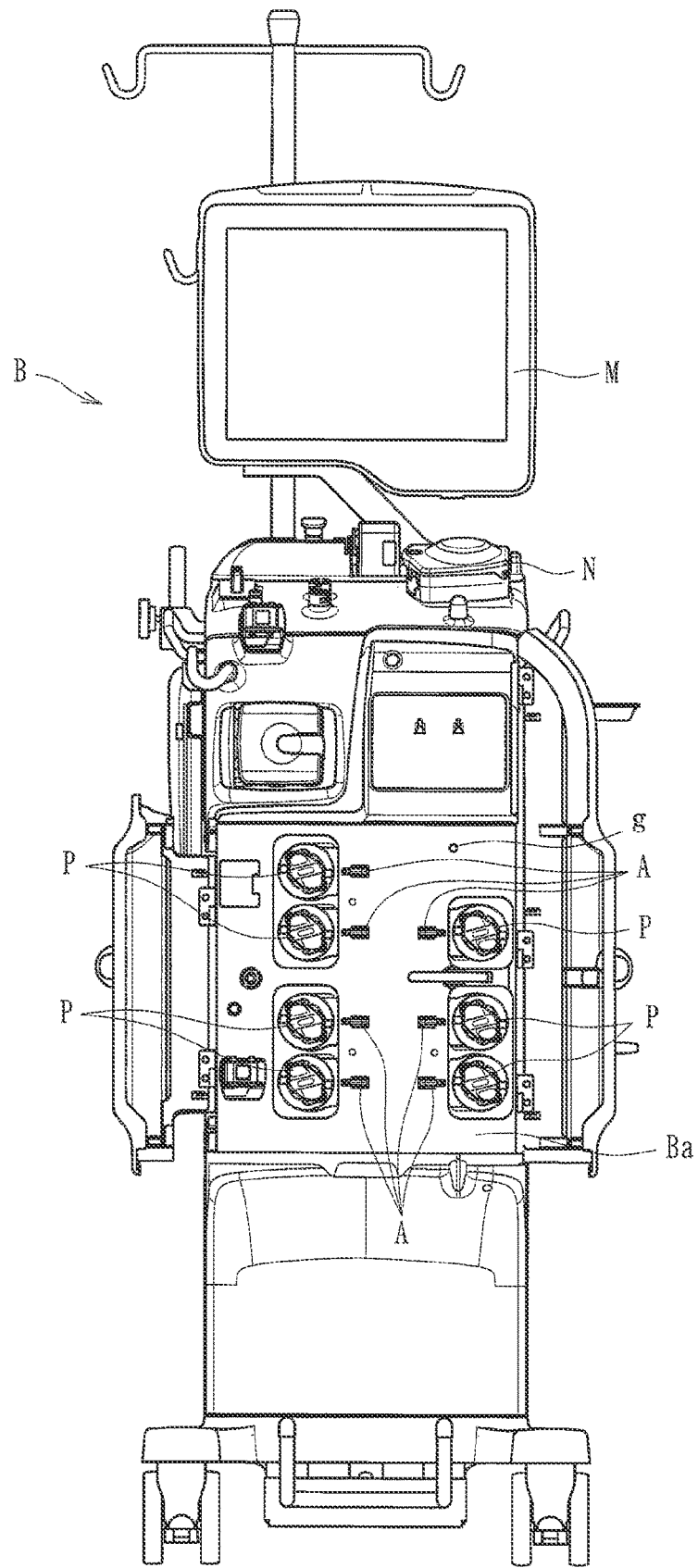

[Fig. 3]
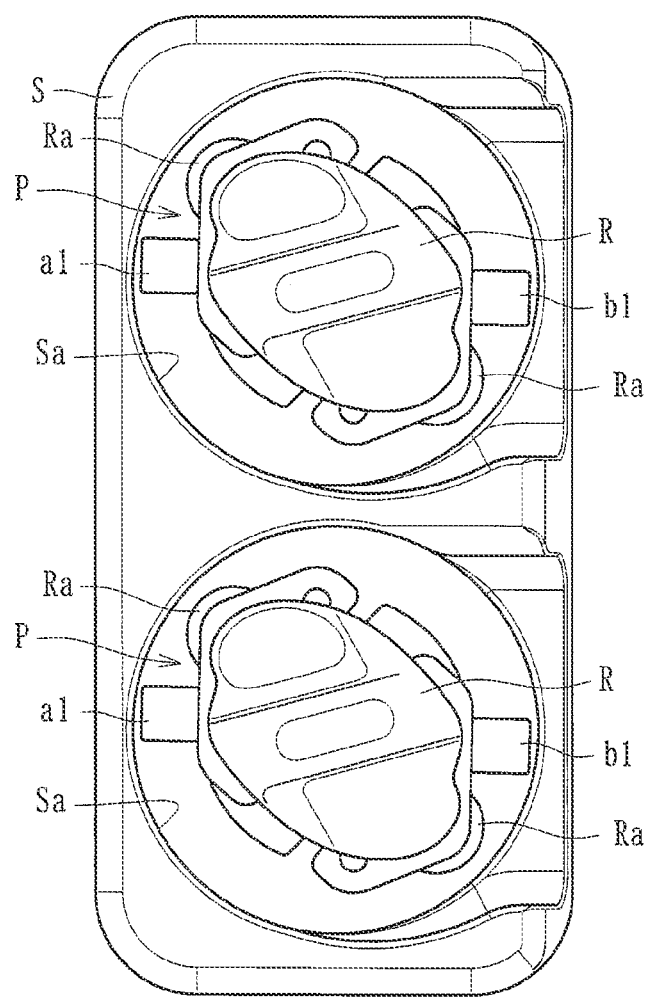

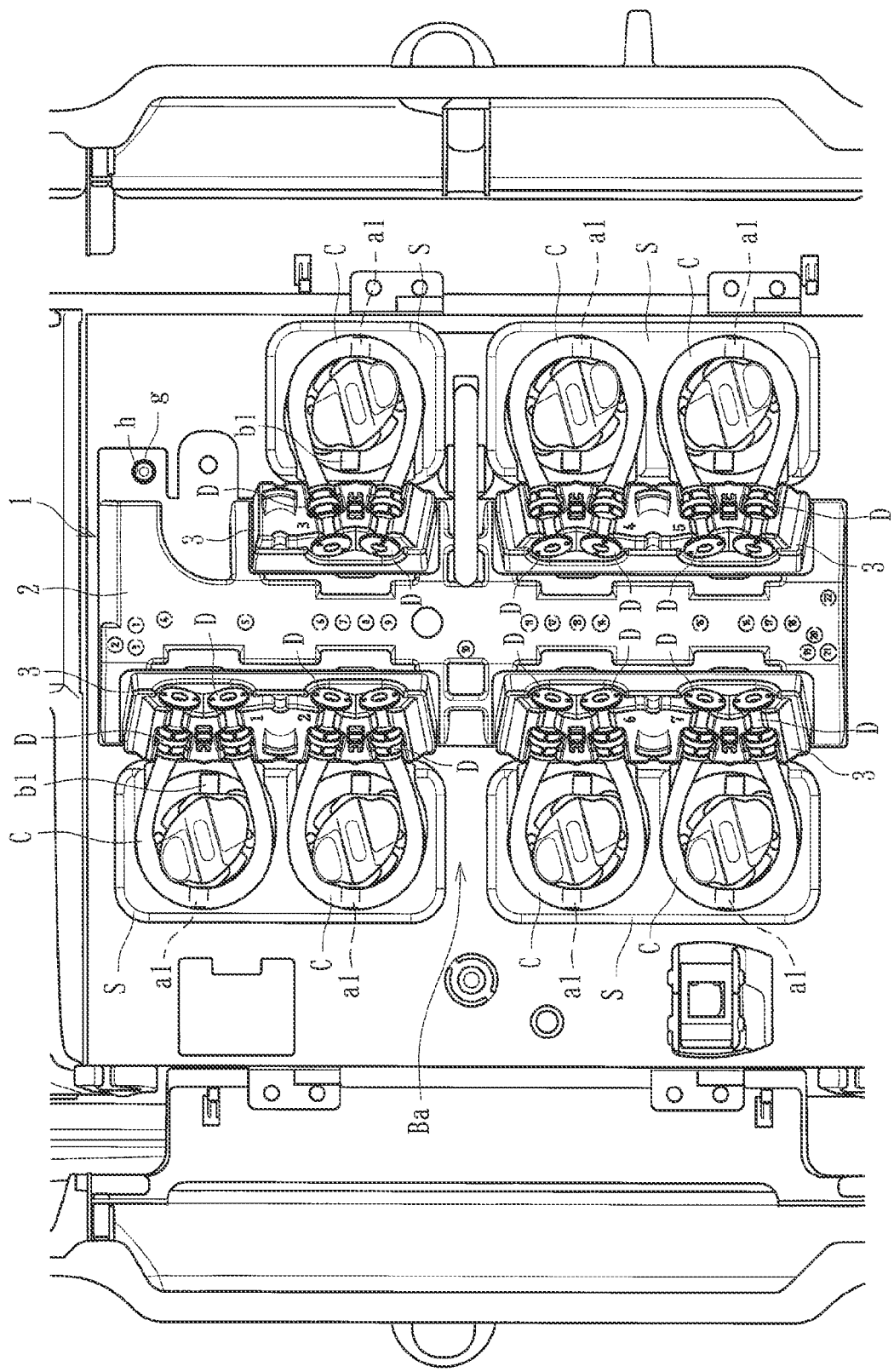

[Fig. 5]
(a)
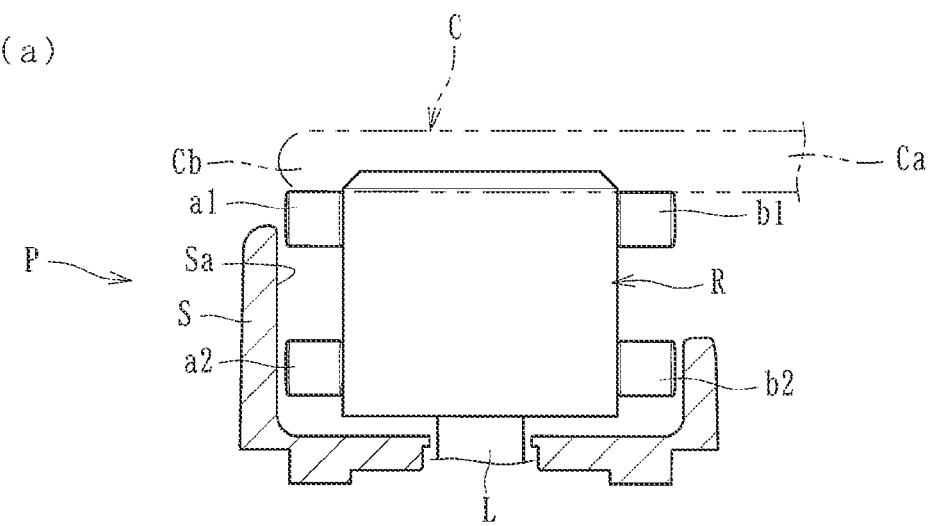
(b)
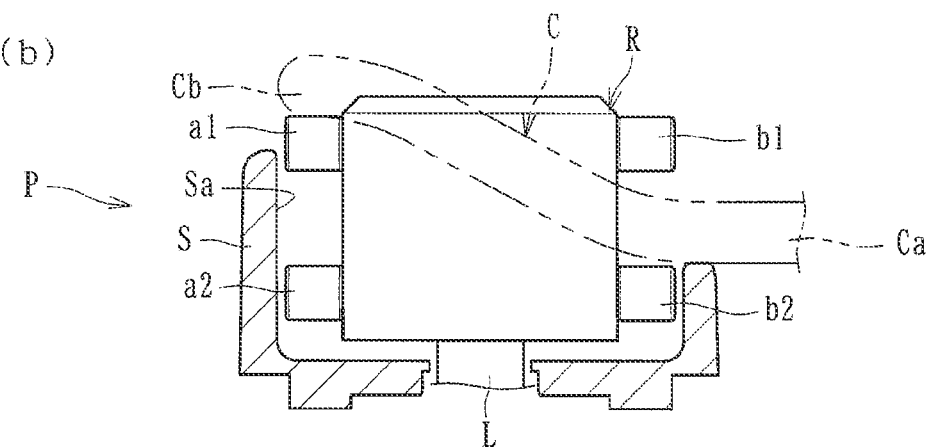
(c)
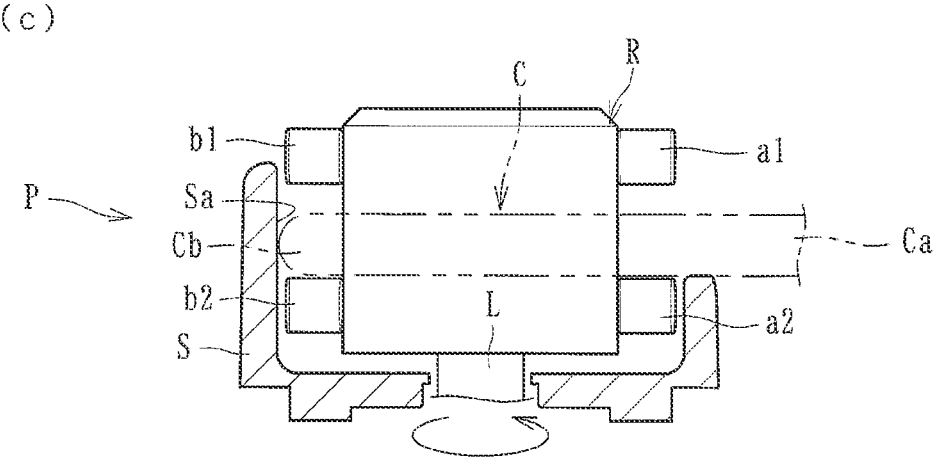

[Fig. 6]
(a)
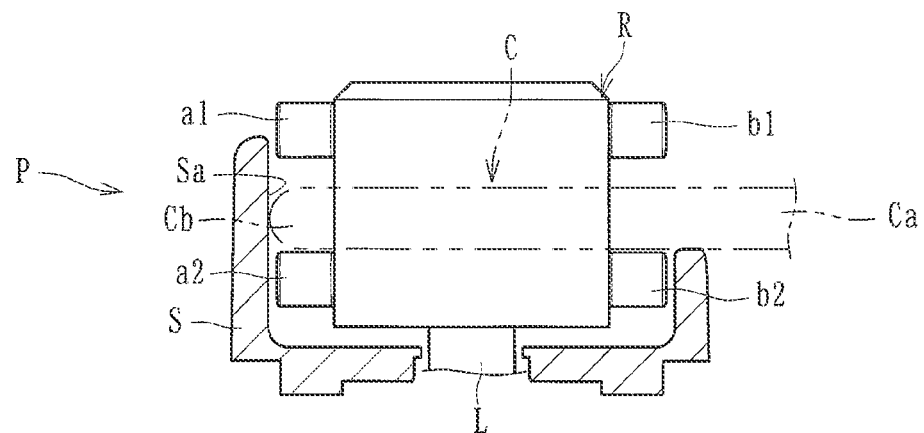
(b)
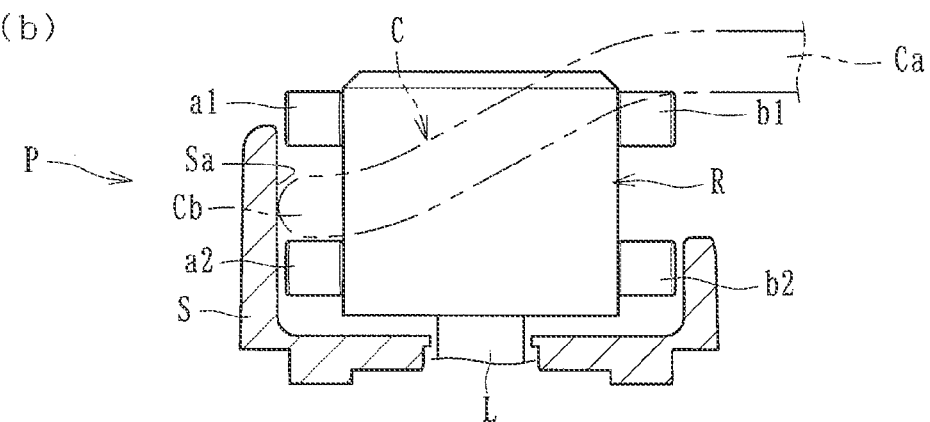
(c)
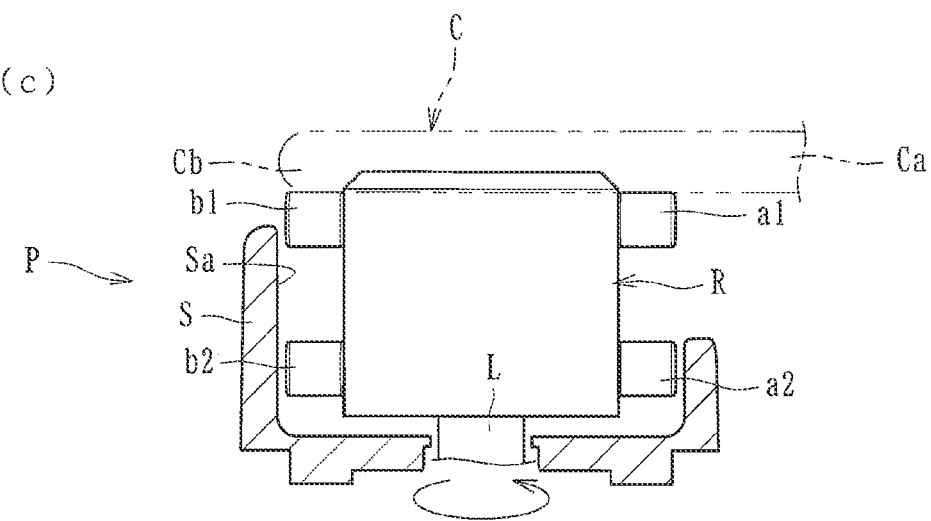

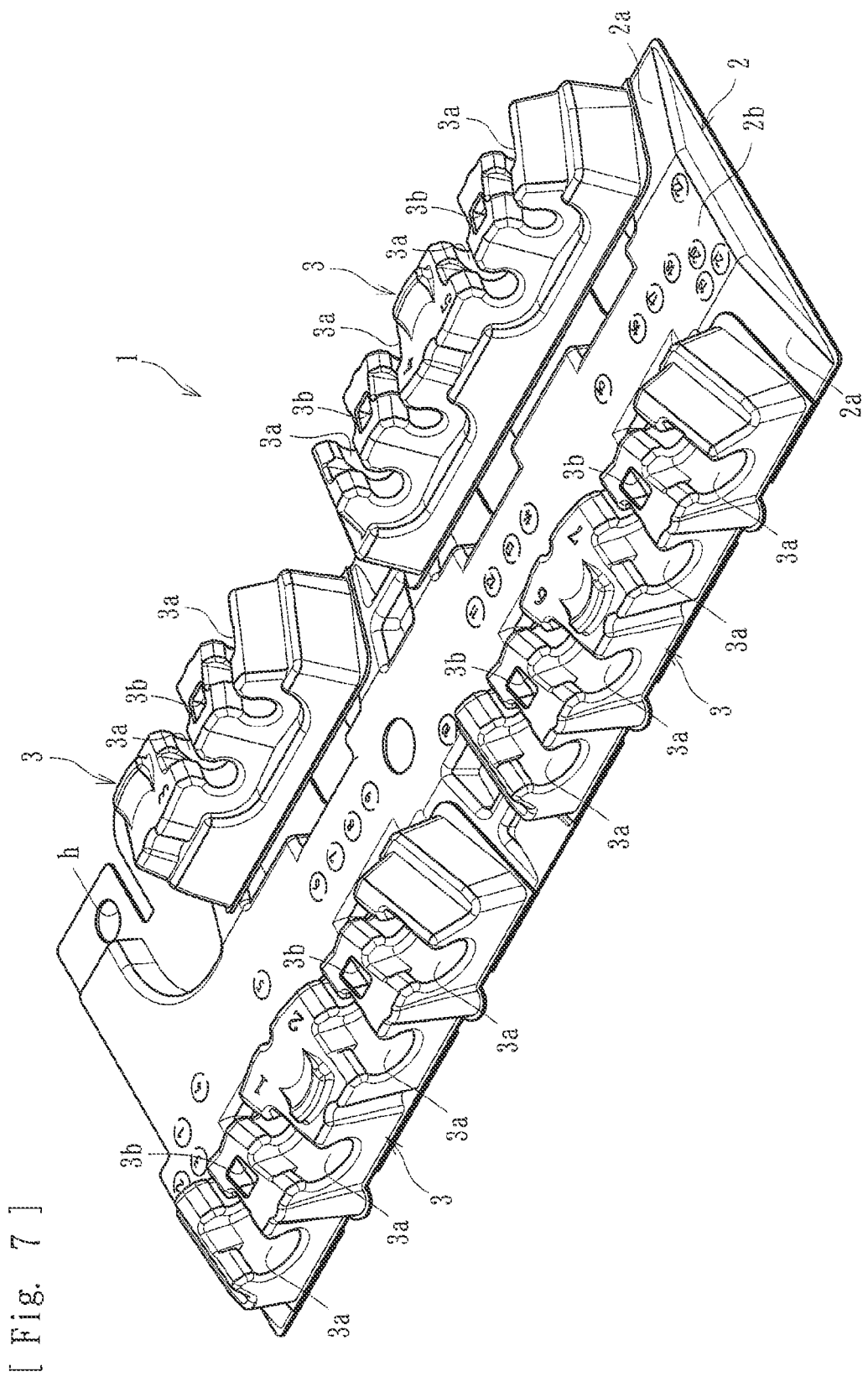
[Fig. 7]

[Fig. 8]
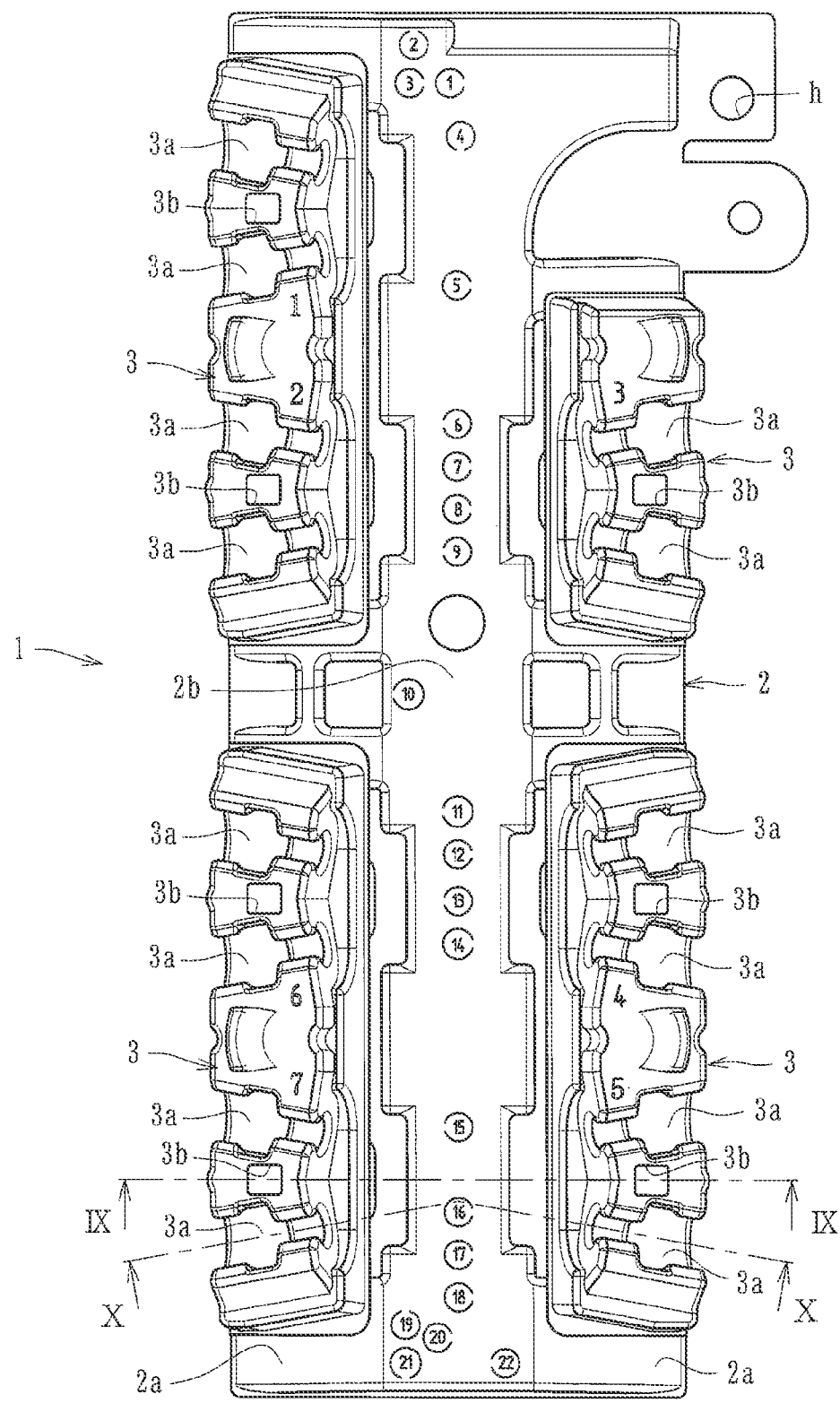

[Fig. 9]
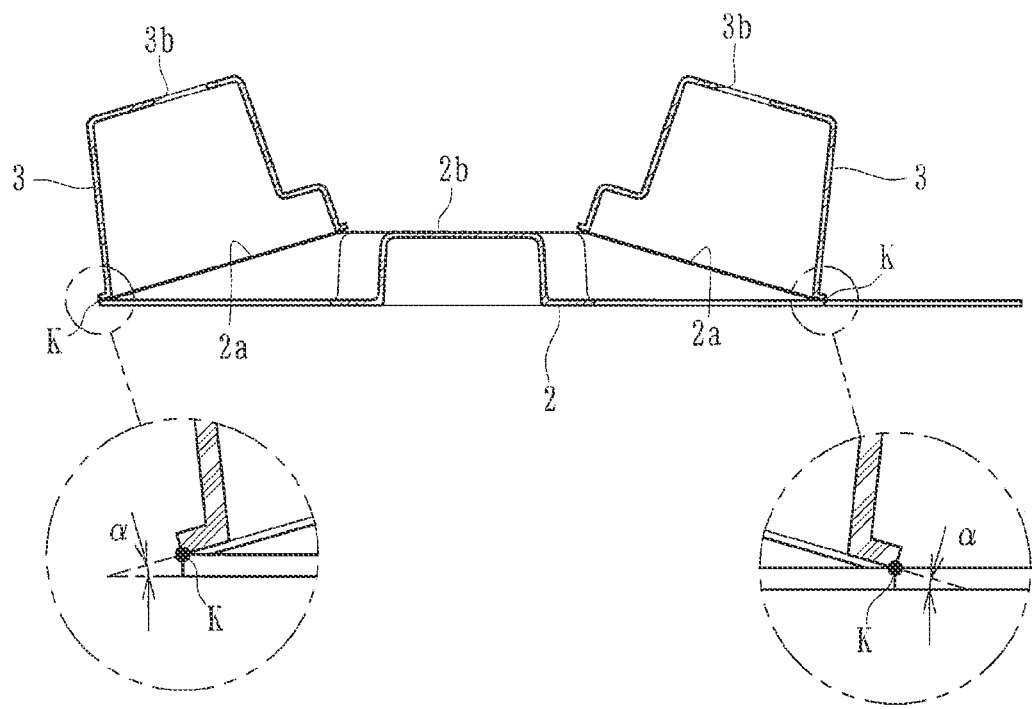
[Fig. 10]
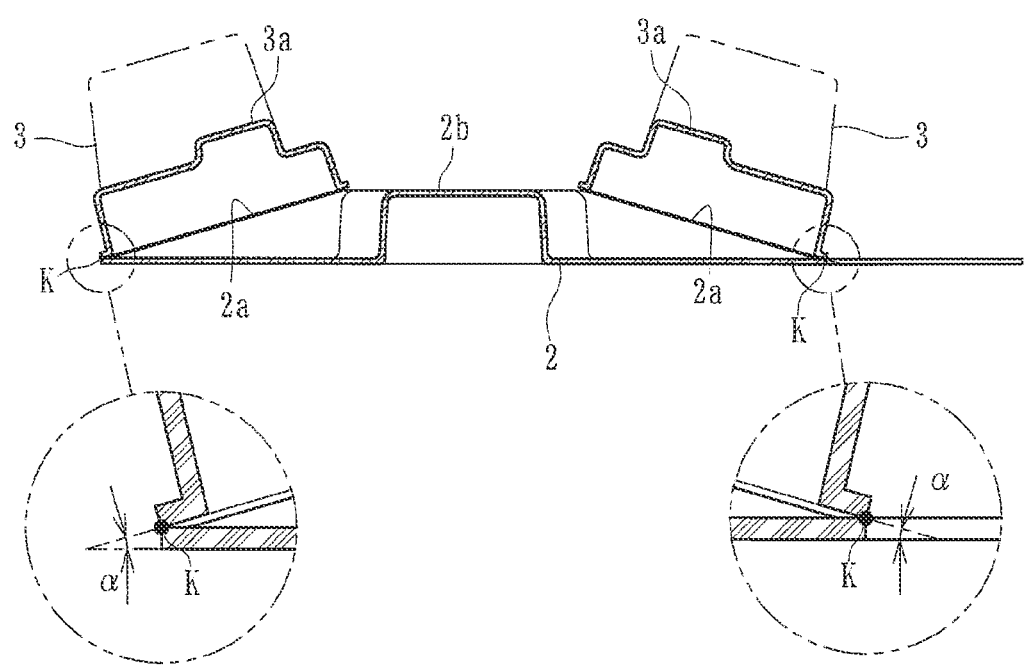

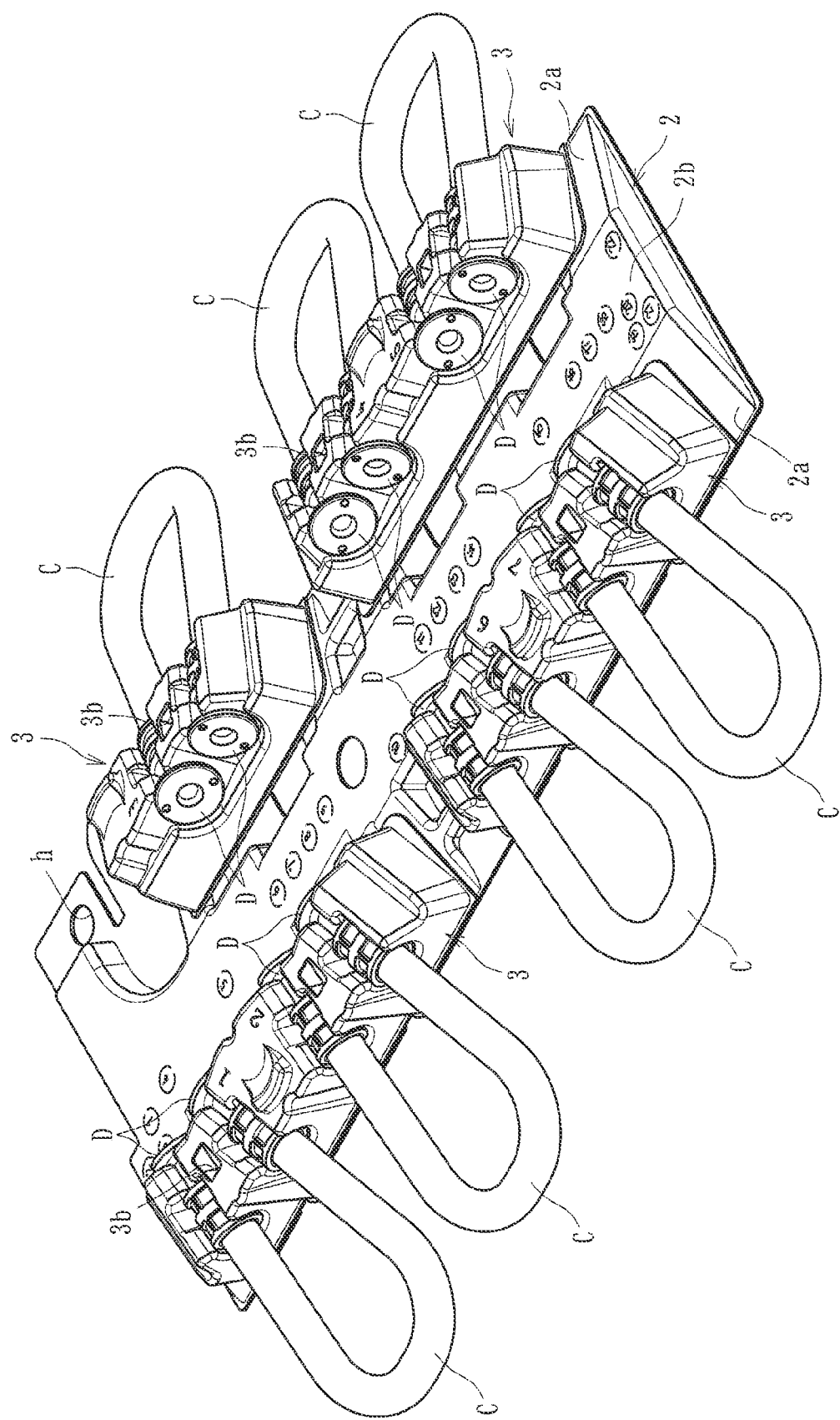
[Fig. 11]

[Fig. 12]
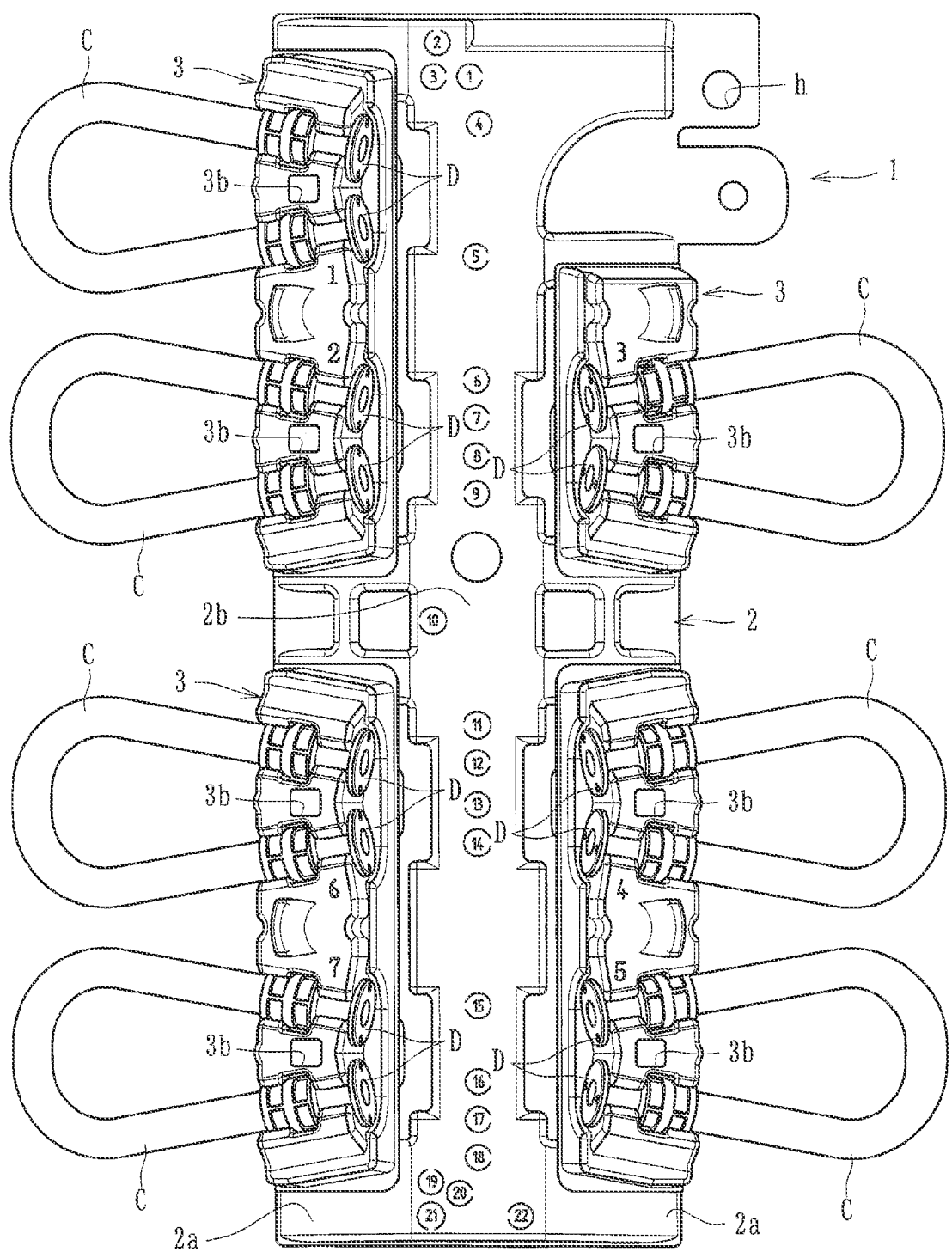

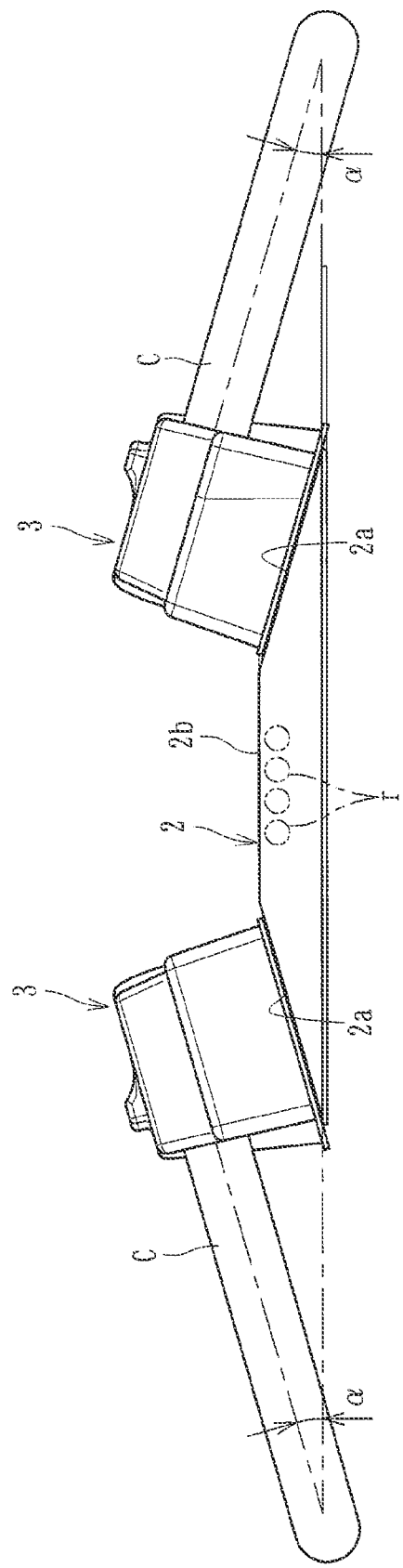
[Fig. 13]

[Fig. 14]
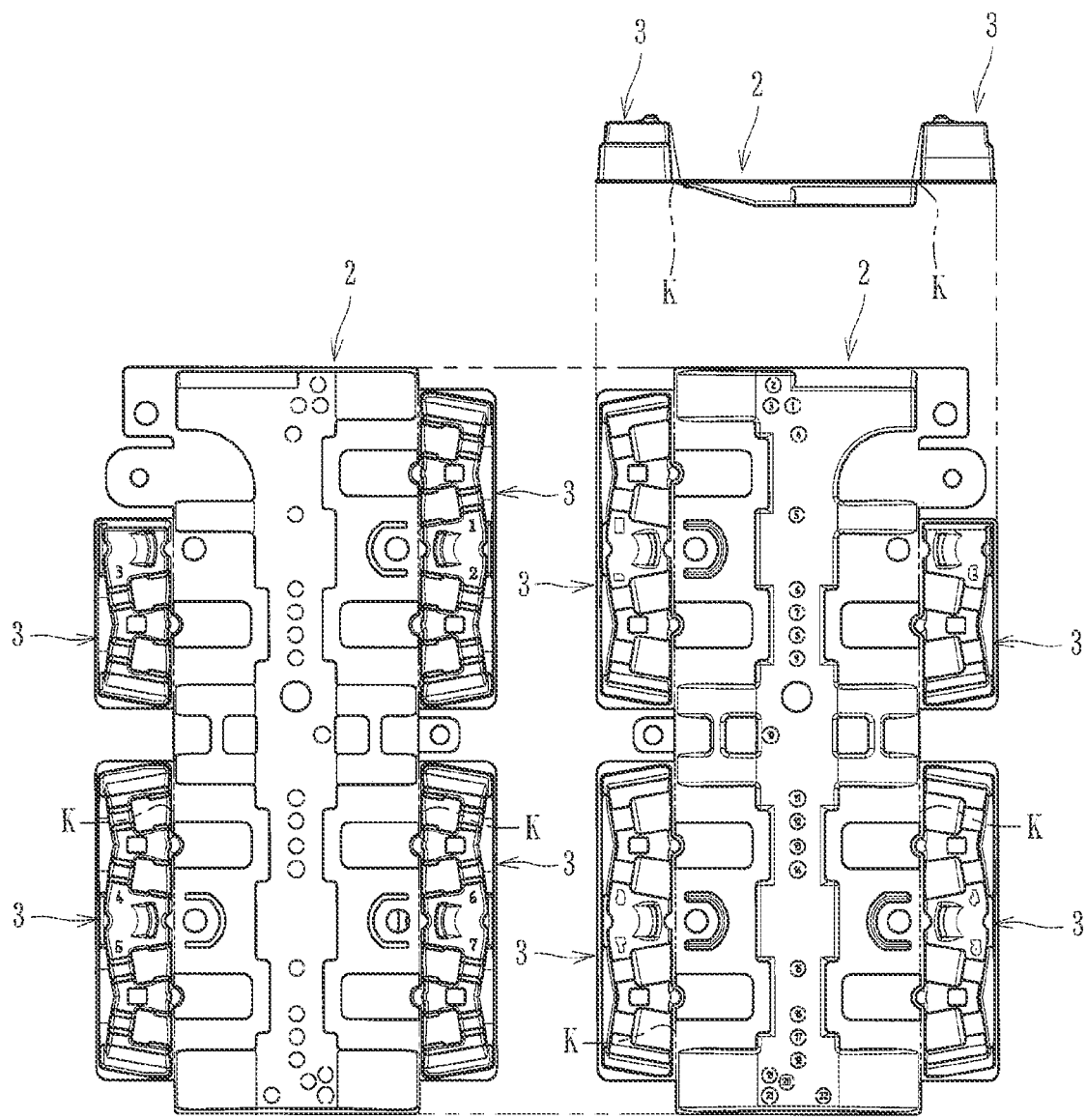

[Fig. 15]
(a)
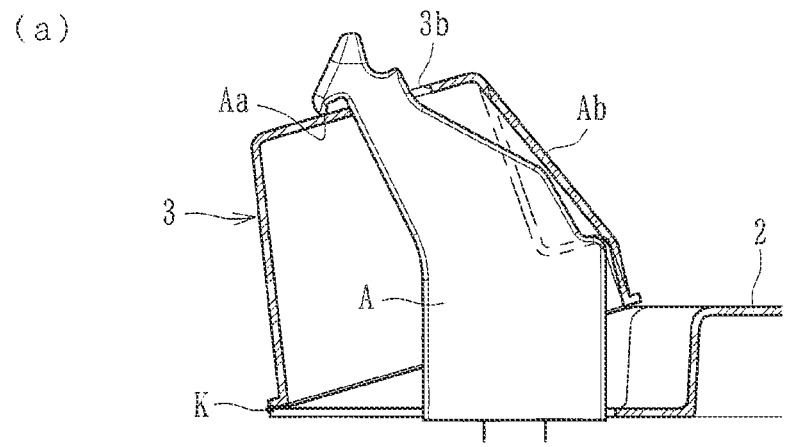
(b)
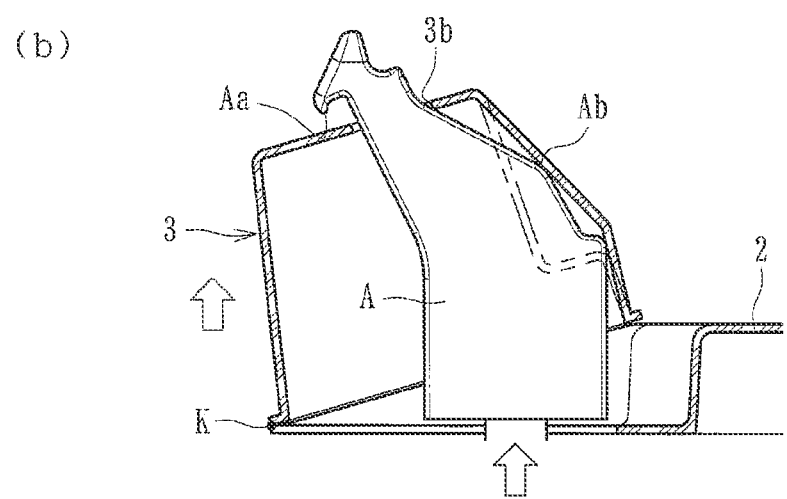
[Fig. 16]
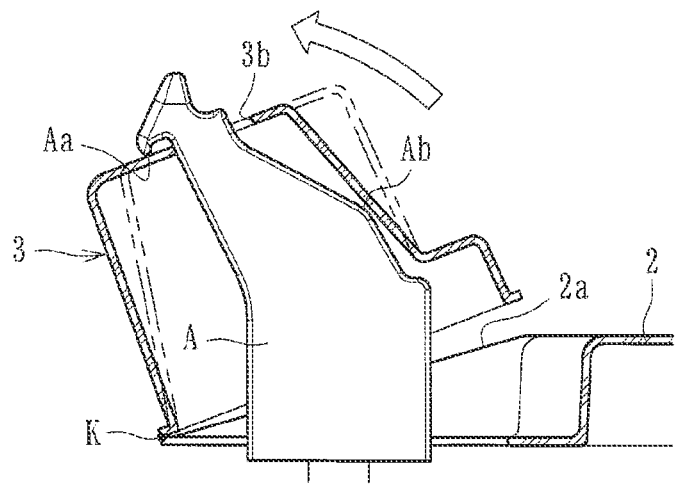

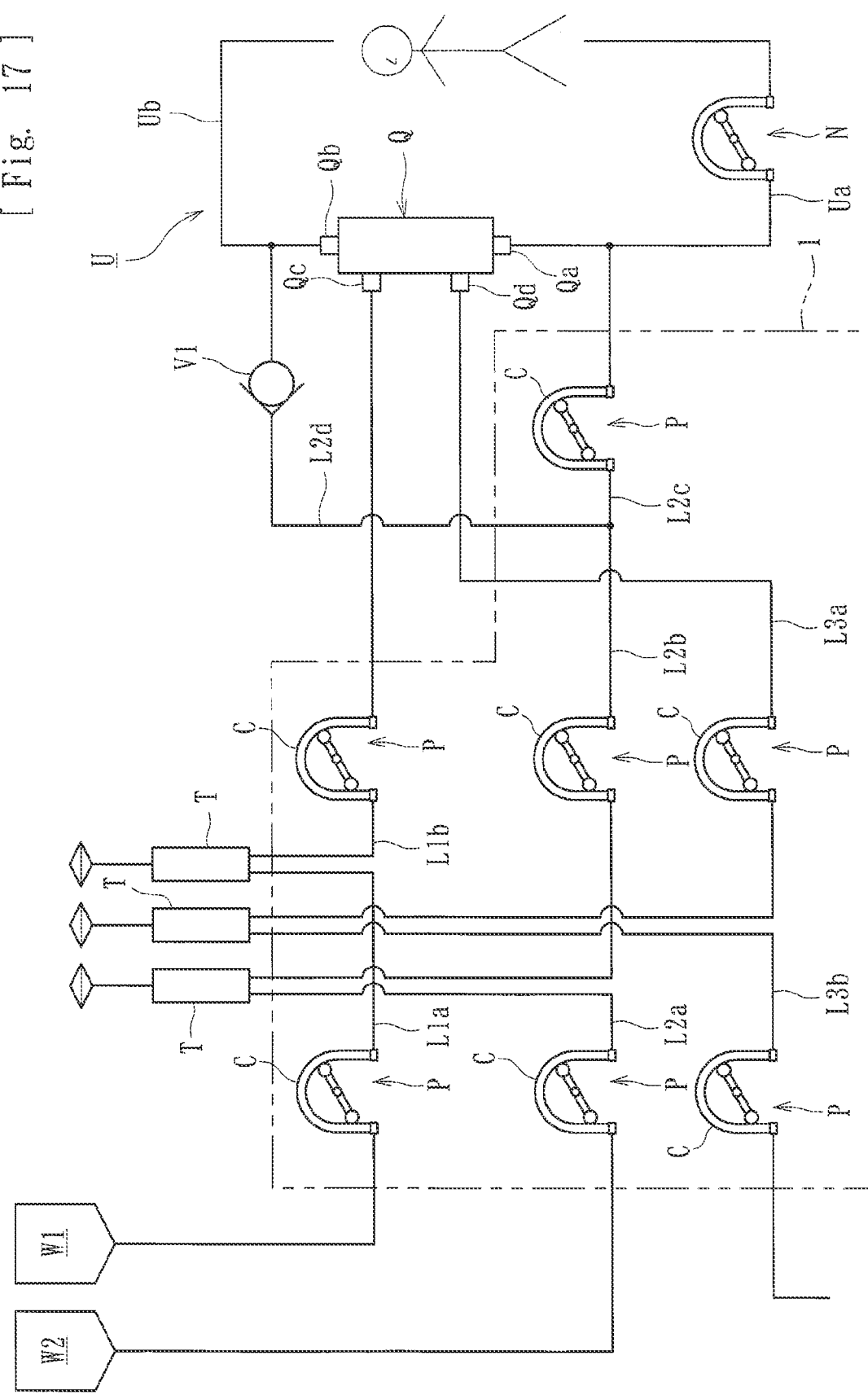

ATTACHING MEMBER

CROSS-REFERENCE TO RELATED APPLICATION(S)

This application is a continuation of International Application No. PCT/JP2019/051338 filed on Dec. 26, 2019, which claims priority to Japanese Application No. 2018-246175, filed on Dec. 27, 2018, the entire disclosures of which are hereby incorporated by reference.

FIELD

The present teachings relate to an attaching member to be attached to a blood purification apparatus including a peristaltic pump, the attaching member holding a pump tube to be squeezed in a predetermined direction by the peristaltic pump for liquid delivery.

BACKGROUND

In general, a blood purification apparatus for giving dialysis treatment is provided with an arterial blood circuit and a venous blood circuit that form a blood circuit for causing blood of a patient to extracorporeally circulate, a blood purifier for purifying the blood extracorporeally circulating through the blood circuit, and various treatment devices, such as a blood pump, for performing blood purification treatment with the blood circuit and the blood purifier. After the patient is punctured with an arterial puncture needle and a venous puncture needle, the blood pump is activated. Thus, blood of the patient flows through the arterial blood circuit and the venous blood circuit. In such a flowing process, the blood is purified by the blood purifier.

Some of blood purification apparatuses according to known proposals each include a plurality of peristaltic pumps for delivering liquids such as substitution fluid and drain liquid. The peristaltic pumps are provided with pump tubes, respectively, so that different liquids can be delivered. Hitherto, for example, an attaching member has been disclosed by PTL 1 that includes a plurality of pump tubes attachable to respective peristaltic pumps included in a blood purification apparatus. The attaching member is to be attached to a predetermined position of the blood purification apparatus.

PTL 1: Japanese Unexamined Patent Application Publication No. 2015-73847, the teachings of which are expressly incorporated by reference herein.

SUMMARY

In the above known attaching member, however, the pump tubes may be deformed in the process of manufacturing, transportation, or the like. For example, a deformation of any of the pump tubes in a direction opposite to the direction in which the pump tubes are attached to the peristaltic pumps may make it difficult to attach or detach such pump tubes to or from the peristaltic pumps.

The present teachings have been conceived in view of the above circumstances and provides an attaching member with which the work of attaching or detaching pump tubes to or from peristaltic pumps can be performed smoothly, regardless of whether the pump tubes are deformed.

Variation 1 may provide an attaching member to be attached to a blood purification apparatus including a peristaltic pump, the attaching member holding a pump tube to be squeezed in a predetermined direction by the peristaltic pump for liquid delivery. The attaching member includes a body attachable to a predetermined position of the blood purification apparatus, and a holding portion attached to the body and that holds the pump tube. The holding portion holds the pump tube such that the pump tube is inclined in a direction in which the pump tube is attached to the peristaltic pump.

Variation 2 may comprise the attaching member according to variation 1, the holding portion holds a connector of the pump tube in an inclined state.

Variation 3 may comprise the attaching member according to variation 1 or 2, the holding portion is displaceable when receiving a load generated at a time of attaching or detaching the pump tube to or from the peristaltic pump.

Variation 4 may comprise the attaching member according to any of variations 1 to 3, the holding portion includes an anchoring part at which the holding portion is anchorable by an anchor member included in the blood purification apparatus; the pump tube is attachable to the peristaltic pump when the holding portion is anchored by the anchor member at the anchoring part; and the pump tube is detachable from the peristaltic pump by moving the anchor member when the anchor member is anchored to the holding portion at the anchoring part.

Variation 5 may comprise a blood purification circuit connected to the pump tube according to any of variations 1 to 4. The blood purification circuit includes a blood circuit through which blood is caused to extracorporeally circulate, and a flow route through which substitution fluid is introduced into the blood circuit or a flow route through which dialysate is introduced into a blood purifier connected to the blood circuit or drain liquid is discharged from the blood purifier.

Variation 1 may comprise the attaching member includes the body attachable to the predetermined position of the blood purification apparatus, and the holding portion attached to the body and that holds the pump tube. The holding portion holds the pump tube such that the pump tube is inclined in the direction in which the pump tube is attached to the peristaltic pump. Therefore, the work of attaching or detaching the pump tube to or from the peristaltic pump can be performed smoothly, regardless of whether the pump tube is deformed.

Variation 2 may comprise the holding portion holds the connector of the pump tube in an inclined state. Therefore, the pump tube can be inclined assuredly when held.

Variation 3 may comprise the holding portion is displaceable when receiving a load generated at the time of attaching or detaching the pump tube to or from the peristaltic pump. Therefore, the work of attaching or detaching the pump tube to or from the peristaltic pump can be performed more stably.

Variation 4 may comprise the holding portion includes the anchoring part at which the holding portion is anchorable by the anchor member included in the blood purification apparatus; the pump tube is attachable to the peristaltic pump when the holding portion is anchored by the anchor member at the anchoring part; and the pump tube is detachable from the peristaltic pump by moving the anchor member when the anchor member is anchored to the holding portion at the anchoring part. Therefore, the work of attaching or detaching the pump tube to or from the peristaltic pump can be automated easily.

According to variation 5, a blood purification circuit that produces the advantageous effects according to variations 1 to 4 can be provided.

BRIEF DESCRIPTION OF THE DRAWINGS

FIG. 1 is an overall diagram of a blood purification apparatus, with an attaching member according to an embodiment of the present invention attached thereto.

FIG. 2 is an overall diagram of the blood purification apparatus, with the attaching member yet to be attached thereto.

FIG. 3 is an enlargement of peristaltic pumps, with pump tubes of the attaching member yet to be attached thereto.

FIG. 4 is an enlargement of a part of the blood purification apparatus, with the attaching member anchored thereto.

FIG. 5 illustrates a process of attaching the pump tube to the peristaltic pump of the blood purification apparatus, including diagram (a) illustrating a state before an anchor member is moved, diagram (b) illustrating a state after the anchor member is moved but before loading is complete, and diagram (c) illustrating a state after loading is complete.

FIG. 6 illustrates a process of detaching the pump tube from the peristaltic pump of the blood purification apparatus, including diagram (a) illustrating a state before the anchor member is moved, diagram (b) illustrating a state after the anchor member is moved but before unloading is complete, and diagram (c) illustrating a state after unloading is complete.

FIG. 7 is a perspective view of the attaching member according to the embodiment.

FIG. 8 is a front view of the attaching member.

FIG. 9 is a sectional view taken along line IX-IX illustrated in FIG. 8.

FIG. 10 is a sectional view taken along line X-X illustrated in FIG. 8.

FIG. 11 is a perspective view of the attaching member, with holding portions thereof holding pump tubes.

FIG. 12 is a front view of the attaching member holding the pump tubes.

FIG. 13 is a side view of the attaching member holding the pump tubes.

FIG. 14 is a third-angle projection of the attaching member, with the holding portions yet to be folded.

FIG. 15 includes diagrams of the attaching member and illustrate a state where the holding portion is anchored by the anchor member at an anchoring part thereof, and a state where the holding portion is pushed by the anchor member.

FIG. 16 is a diagram of the attaching member and illustrates a state where the holding portion is rocked relative to a body.

FIG. 17 is a diagram illustrating a blood purification apparatus with the attaching member attached thereto, and is provided for describing blood purification treatment.

DETAILED DESCRIPTION

Embodiments of the present invention will now be described specifically with reference to the drawings.

An attaching member according to an embodiment is to be attached to a blood purification apparatus including peristaltic pumps. The attaching member holds pump tubes to be squeezed in a predetermined direction by the respective peristaltic pumps for liquid delivery. As illustrated in FIGS. 1 to 13, the attaching member includes a body 2 attachable to a predetermined position Ba of a blood purification apparatus B, and holding portions 3 attached to the body 2 and that hold pump tubes C.

As illustrated in FIG. 14, the attaching member 1 is a resin molded component in which the body 2 and the holding portions 3 are formed continuously with each other. When the component is folded at folds K extending along the boundaries between the body 2 and the holding portions 3, the holding portions 3 are placed on the front face of the body 2 as illustrated in FIG. 7. The folds K each have perforations or the like. Therefore, the holding portions 3 are easily foldable with respect to the body 2.

As illustrated in FIGS. 7 to 13, the body 2 according to the present embodiment is a rectangular resin molded part and has inclined surfaces 2a provided on two opposite sides thereof, respectively. The inclined surfaces 2a are each inclined at a predetermined angle α with respect to the bottom surface of the body 2 (an attaching surface that faces the predetermined position Ba). Furthermore, the body 2 includes a central portion 2b positioned in the center thereof and between the left and right inclined surfaces 2a. Specifically, the body 2 has the central portion 2b in the center thereof, with the inclined surfaces 2a at the angle α extending from the central portion 2b toward the left and right sides, respectively. The inclined surfaces 2a carry a plurality of (four in the present embodiment) holding portions 3.

The holding portions 3 are each a resin molded part projecting in a block-like shape from the body 2 (projecting frontward). As illustrated in FIGS. 11 and 12, the holding portions 3 have holding grooves 3a, into each of which one of connectors D provided at two respective ends of each of the pump tubes C is to be fitted, whereby the connectors D are securable at a predetermined height. In short, the connectors D are secured by being fitted into the holding grooves 3a, whereby the pump tubes C are held by the holding portions 3 as illustrated in FIGS. 11 to 13. Furthermore, as illustrated in FIG. 9, the holding portions 3 have anchoring holes 3b (anchoring parts) in predetermined areas thereof and are therefore anchorable by anchor members A included in the blood purification apparatus B.

The pump tubes C are each made of a material such as soft resin or rubber forming a flow route with a relatively large diameter. Each pump tube C has the connectors D at one end and the other end thereof, respectively. After the pump tubes C are fitted into respective stators S of the peristaltic pumps P, respective rotors R are driven to rotate. Thus, the pump tubes C are squeezed in the lengthwise direction by rollers Ra, so that liquids such as substitution fluid and drain liquid can be delivered.

As illustrated in FIGS. 9, 10, and 13, the holding portions 3 according to the present embodiment are provided on the inclined surfaces 2a. Therefore, the pump tubes C each extend at the predetermined angle α (inclined along the inclined surface 2a) with respect to the bottom surface of the body 2 (the attaching surface that faces the predetermined position Ba). In other words, the holding portions 3 according to the present embodiment hold the connectors D of the pump tubes C in an inclined state. Specifically, the holding portions 3 hold the pump tubes C such that the pump tubes C are inclined in a direction in which the pump tubes C are attached to the peristaltic pumps P (a downward direction in FIG. 13).

The body 2 according to the present embodiment is configured such that tubes (r) forming liquid flow routes connected to the connectors D of the pump tubes C are placed in the central portion 2b thereof. Specifically, the central portion 2b of the body 2 according to the present embodiment has a concavity that is open on the rear side, and the tubes (r) connected to the connectors D of the pump tubes C are placed along the concavity.

As illustrated in FIGS. 1 to 3, the blood purification apparatus B applied to the present embodiment is a monitoring apparatus for hemodialysis treatment that includes a monitor M capable of displaying information regarding blood purification treatment and the like, a blood pump N, and so forth. When the blood pump N is activated, blood of a patient is caused to extracorporeally circulate through a blood circuit. Meanwhile, the blood undergoes blood purification treatment in a blood purifier (a dialyzer). The blood purification apparatus B according to the present embodiment includes a plurality of (seven in the present embodiment) peristaltic pumps P provided on the front face thereof, so that substitution fluid and drain liquid can be delivered in the blood purification treatment.

The peristaltic pumps P are each capable of delivering liquid by squeezing the pump tube C in a specific direction and each include, as illustrated in FIGS. 3 to 6, the stator S having a fitting recess Sa, the rotor R provided in the fitting recess Sa and being rotatable about a rotating shaft L, and the rollers Ra provided on the rotor R. When the pump tube C is fitted into the fitting recess Sa of the stator S and the rotor R is driven to rotate, the pump tube C is squeezed between the wall of the fitting recess Sa and the rollers Ra. Thus, the liquid can be delivered.

The rotor R has an upper guide pin a1 and a lower guide pin a2 provided in a pair, and an upper guide pin b1 and a lower guide pin b2 provided in a pair, all of which project from the rotor R. The pump tube C is to be fitted between the upper guide pin a1 and the lower guide pin a2 and between the upper guide pin b1 and the lower guide pin b2. The upper guide pins a1 and b1 are positioned on the open side of the fitting recess Sa. The lower guide pins a2 and b2 are positioned on the bottom side of the fitting recess Sa. Thus, displacement of the pump tube C fitted in the fitting recess Sa from a predetermined position (a position where the pump tube C is squeezable by the rollers Ra) is suppressed.

The blood purification apparatus B according to the present embodiment receives the attaching member 1 attachable to the predetermined position Ba on the front face thereof, where the peristaltic pumps P are provided. Specifically, as illustrated in FIG. 4, the blood purification apparatus B according to the present embodiment has a positioning pin (g). When the positioning pin (g) is inserted into a positioning hole (h) provided in the body 2 of the attaching member 1, the attaching member 1 can be positioned at the predetermined position Ba of the blood purification apparatus B.

As illustrated in FIG. 2, the blood purification apparatus B according to the present embodiment further has a plurality of anchor members A at the predetermined position Ba. Meanwhile, as described above, the holding portions 3 have the anchoring holes 3b (the anchoring parts) at which the holding portions 3 are anchorable by the anchor members A. As illustrated in FIGS. 15 and 16, the anchor members A each include an anchor hook Aa on one side of the distal end thereof, and a pushing portion Ab on the other side. The anchor hook Aa is hooked on the peripheral edge of the anchoring hole 3b (see FIG. 15(a)). Thus, the attaching member 1 is anchored by the anchor member A and is secured to the predetermined position Ba.

In a state where the attaching member 1 is positioned by the positioning pin (g) and is anchored at the anchoring holes 3b (the anchoring parts) by the anchor hooks Aa of the anchor members A (see FIG. 15(a)), as illustrated in FIG. 5(a), proximal portions Ca and a distal portion Cb of each of the pump tubes C held by the holding portions 3 are positioned above the upper guide pins a1 and b1 of a corresponding one of the peristaltic pumps P. Meanwhile, the rotor R of each of the peristaltic pumps P is stopped at a predetermined position (see FIGS. 2 to 4). In such an anchoring state, the anchor member A is moved in such a direction as to sink into the predetermined position Ba (a direction in which the attaching member 1 is moved toward the predetermined position Ba). Then, as illustrated in FIG. 5(b), the proximal portions Ca of the pump tube C are positioned between the upper guide pin b1 and the lower guide pin b2, while the distal portion Cb of the pump tube C is positioned above the upper guide pin a1.

In such a state, the rotor R is driven to rotate. Then, as illustrated in FIG. 5(c), while the proximal portions Ca of the pump tube C are positioned between the upper guide pin a1 and the lower guide pin a2, the distal portion Cb of the pump tube C interferes with the upper guide pin b1 and is drawn to a position between the upper guide pin b1 and the lower guide pin b2. Thus, the pump tube C is set in the peristaltic pump P. Such attaching work of setting the pump tube C by drawing the pump tube C to the position between the upper guide pin a1 and the lower guide pin a2 is also referred to as loading.

On the other hand, in the state where the pump tube C is set in the peristaltic pump P as illustrated in FIG. 6(a) with the anchor member A anchoring at the anchoring hole 3b (the anchoring part), the anchor member A is moved in a direction of projection thereof (a direction in which the attaching member 1 is lifted from the predetermined position Ba). Then, the pushing portion Ab of the anchor member A pushes the peripheral edge of the anchoring hole 3b (see FIG. 15(b)) and lifts the pump tube C from the fitting recess Sa. Meanwhile, the rotor R of each of the peristaltic pumps P is stopped at the same predetermined position (see FIGS. 2 to 4) as in the case of the loading of the pump tube. Furthermore, as illustrated in FIG. 6(b), the distal portion Cb of the pump tube C is positioned between the upper guide pin a1 and the lower guide pin a2, while the proximal portions Ca of the pump tube C are positioned above the upper guide pin b1.

In such a state, the rotor R is driven to rotate. Then, as illustrated in FIG. 6(c), while the proximal portions Ca of the pump tube C are positioned above the upper guide pin a1, the distal portion Cb of the pump tube C interferes with the upper guide pin b1 and is pushed to a position above the upper guide pin b1. Thus, the pump tube C that has been set in the peristaltic pump P is unset and is allowed to be detached. Such detaching work of unsetting the pump tube C by pushing out the pump tube C from the position between the upper guide pin a1 and the lower guide pin a2 is also referred to as unloading.

The holding portions 3 of the attaching member 1 according to the present embodiment are displaceable relative to the body 2. If a load occurs on any of the pump tubes C that are being attached to or detached from the peristaltic pumps P, a corresponding one of the holding portions 3 rocks in such a direction as to release the load. Thus, the holding portion 3 is displaceable relative to the body 2. Specifically, the holding portions 3 are each rockable about the fold K relative to the body 2. If a load occurs on any of the pump tubes C, the corresponding holding portion 3 rocks in such a direction as to be pulled from the body 2, whereby the load is released.

For example, if a load occurs on any of the pump tubes C in the process of loading the pump tubes C onto the peristaltic pumps P in fitting the pump tubes C to the peristaltic pumps P, a corresponding one of the holding portions 3 rocks about the fold K as illustrated in FIG. 16. Thus, the load can be released. Even if a load occurs with the interference between the anchor member A and the peripheral edge of the anchoring hole 3b in the process of inserting the anchor member A into the anchoring hole 3b of the holding portion 3, the holding portion 3 rocks about the fold K as illustrated in the drawing. Thus, the load can be released.

On the other hand, if a load occurs on any of the pump tubes C in the process of unloading the pump tubes C from the peristaltic pumps P in removing the pump tubes C from the peristaltic pumps P, a corresponding one of the holding portions 3 rocks about the fold K as illustrated in FIG. 16. Thus, the load can be released. Even if a load occurs with the interference between the pump tube C and the rotor R or the like of the peristaltic pump P during the blood purification treatment, the holding portion 3 rocks about the fold K as illustrated in the drawing. Thus, the load can be released.

When the attaching member 1 is anchored to the predetermined position Ba of the blood purification apparatus B and the pump tubes C are loaded onto the respective peristaltic pumps P, a treatment apparatus for blood purification treatment is established as illustrated in FIG. 17. The treatment apparatus includes a blood circuit U including a dialyzer Q; a first dialysate introduction line L1a and a second dialysate introduction line L1b through which dialysate is introduced into the dialyzer Q; a first substitution line L2a, a second substitution line L2b, a pre-substitution line L2c, and a post-substitution line L2d through which substitution fluid is supplied to the blood circuit U; and a first drain-liquid discharge line Lia and a second drain-liquid discharge line L3b through which drain liquid is discharged from the dialyzer Q.

The blood circuit U includes an arterial blood circuit Ua and a venous blood circuit Ub. When the blood pump N is activated while a patient is punctured with the distal ends of the arterial blood circuit Ua and the venous blood circuit Ub, blood of the patient can be caused to extracorporeally circulate. The dialyzer Q has a blood introduction port Qa, a blood delivery port Qb, a dialysate introduction port Qc, and a dialysate delivery port Qd all projecting from a housing thereof. The arterial blood circuit Ua is connected to the blood introduction port Qa. The venous blood circuit Ub is connected to the blood delivery port Qb. The second dialysate introduction line L1b is connected to the dialysate introduction port Qc. The first drain-liquid discharge line L3a is connected to the dialysate delivery port Qd.

The first dialysate introduction line Da is connected to a dialysate bag W1 that stores dialysate and is also connected to the second dialysate introduction line L1b through a temporary chamber T. When the peristaltic pumps P provided to the first dialysate introduction line L1a and the second dialysate introduction line L1b are activated, the dialysate in the dialysate bag W1 is temporarily stored in the temporary chamber T and is then introduced into the dialyzer Q.

The first substitution L2a is connected to a substitution-fluid bag W2 that stores substitution fluid and is also connected to the second substitution line L2b through a temporary chamber T. The second substitution line L2b is connected to the blood circuit U through the pre-substitution line L2c connected to the arterial blood circuit Ua and through the post-substitution line L2d connected to the venous blood circuit Ub. The post-substitution line L2d is provided with a check valve V1. When the peristaltic pumps P provided to the first substitution line L2a and the second substitution line L2b are activated, the substitution fluid in the substitution-fluid bag W2 is temporarily stored in the temporary chamber T and is then introduced into the arterial blood circuit Ua or the venous blood circuit Ub in accordance with the state of operation of the peristaltic pump P provided to the pre-substitution line L2c.

The first drain-liquid discharge line L3a is connected to the dialyzer Q and is also connected to the second drain-liquid discharge line L3b through a temporary chamber T. The second drain-liquid discharge line L3b allows the drain liquid to be discharged therethrough to the outside of the apparatus. When the peristaltic pumps P provided to the first drain-liquid discharge line L3a and the second drain-liquid discharge line L3b are activated, the drain liquid in the dialyzer Q is temporarily stored in the temporary chamber T and is then allowed to be discharged to the outside of the apparatus.

As described above, the pump tubes C of the attaching member 1 are connected to the flow routes (the first substitution line L2a, the second substitution line L2b, and the pre-substitution line L2c) through which the substitution fluid is introduced into the blood circuit U, the flow routes (the first dialysate introduction line L1a and the second dialysate introduction line L1b) through which the dialysate is introduced into the dialyzer Q (a blood purifier) connected to the blood circuit U, and the flow routes (the first drain-liquid discharge line L3a and the second drain-liquid discharge line L3b) through which the drain liquid is discharged from the dialyzer Q (the blood purifier). The post-substitution line L2d may also be connected to one of the pump tubes C of the attaching member 1.

In the present embodiment, none of the pump tubes C of the attaching member 1 is attached to the blood pump N. Alternatively, one of the pump tubes C of the attaching member 1 may be attached to the blood pump N by loading the pump tube C thereon. In such a case, what is to be connected to the pump tube C of the attaching member 1 is the blood circuit U. That is, devices that are loadable onto the pump tubes C of the attaching member 1 according to the present invention include a blood purification circuit that includes the following: the blood circuit U through which the blood is caused to extracorporeally circulate; and the flow routes (the first substitution line L2a, the second substitution line L2b, and the pre-substitution line L2c (or the post-substitution line L2d)) through which the substitution fluid is introduced into the blood circuit U, the flow routes (the first dialysate introduction line Da and the second dialysate introduction line L1b) through which the dialysate is introduced into the dialyzer Q (the blood purifier) connected to the blood circuit U, or the flow routes (the first drain-liquid discharge line L3a and the second drain-liquid discharge line L3b) through which the drain liquid is discharged from the dialyzer Q (the blood purifier).

According to the above embodiment, the attaching member 1 includes the body 2 attachable to the predetermined position Ba of the blood purification apparatus B, and the holding portions 3 attached to the body 2 and that hold the pump tubes C. The holding portions 3 hold the pump tubes C such that the pump tubes C are inclined in the direction in which the pump tubes C are attached to the peristaltic pumps P. Therefore, the work of attaching or detaching the pump tubes C to or from the peristaltic pumps can be performed smoothly, regardless of whether the pump tubes C are deformed. Note that the direction in which the pump tubes P are attached to the peristaltic pumps P specifically refers to a direction toward the bottoms of the stators S of the peristaltic pumps P.

More specifically, even if any of the pump tubes C are deformed and bent in a direction opposite to the direction in which the pump tubes C are attached to the peristaltic pumps P in the process of manufacturing, transportation, or the like of the attaching member, the bend in the opposite direction is cancelled out or absorbed by the inclination of the pump tubes C when the body 2 is attached to the blood purification apparatus B. That is, the pump tubes C are always oriented in the direction in which the pump tubes P are attached (the direction toward the bottoms of the stators S). Therefore, the work of attaching or detaching the pump tubes C to or from the peristaltic pumps P can be performed smoothly.

The holding portions 3 according to the present embodiment hold the connectors D of the pump tubes C in an inclined state. Therefore, the pump tubes C can be inclined assuredly when held. Furthermore, the holding portions 3 according to the present embodiment are displaceable (rockable) when receiving a load generated at the time of attaching or detaching the pump tubes C to or from the peristaltic pumps P. Therefore, the work of attaching or detaching the pump tubes C to or from the peristaltic pumps P can be performed more stably. The holding portions 3 according to the present embodiment are rockable when receiving a load generated at the time of attaching or detaching the pump tubes C to or from the peristaltic pumps P. Alternatively, the holding portions 3 may undergo another motion (sliding, expansion/contraction, or the like), instead of rocking.

The holding portions 3 according to the present embodiment have the anchoring holes 3b (the anchoring parts) at which the holding portions 3 are anchorable by the anchor members A included in the blood purification apparatus B. The pump tubes C are attachable to the peristaltic pumps P when the holding portions 3 are anchored by the anchor members A at the anchoring holes 3b. Furthermore, the pump tubes C are detachable from the peristaltic pumps P when the anchor members A that are anchoring the holding portions 3 at the anchoring holes 3b are moved. Therefore, the work of attaching or detaching the pump tubes C to or from the peristaltic pumps P can be automated easily.

The holding portions 3 according to the present embodiment are each displaceable by rocking relative to the body 2. Therefore, a load occurring on any of the pump tubes C that are being attached or detached can be released with the rocking of the holding portions 3 relative to the body 2. Furthermore, the holding portions 3 according to the present embodiment are each continuous with and folded with respect to the body 2 and are each rockable about the fold K. That is, the attaching member 1 can be obtained by forming the body 2 and the holding portions 3 continuously with each other and then folding the holding portions 3. Therefore, the attaching member 1 can be manufactured easily.

While an embodiment has been described above, the present invention is not limited thereto. For example, a plurality of, but not seven, peristaltic pumps P or a single peristaltic pump P may be provided on the blood purification apparatus B, and a number of pump tubes C that corresponds to the number of peristaltic pumps P may be held by the holding portions 3. The attaching member 1 according to the above embodiment is anchored by the anchor members A included in the blood purification apparatus B and is configured such that the pump tubes C are unloaded from the peristaltic pumps P by moving the anchor members A in the direction of projection thereof. The anchor members A may be moved by actuators, by hand, or by any other means.

The holding portions 3 according to the above embodiment are each continuous with and folded with respect to the body 2 and are each rockable about the fold K. Alternatively, the holding portions 3 may be formed on the body 2 continuously therewith in such a manner as not to be rockable (displaceable). In such a case as well, if the holding portions 3 hold the pump tubes C such that the pump tubes C are inclined in the direction in which the pump tubes C are attached to the peristaltic pumps P, the work of attaching or detaching the pump tubes C to or from the peristaltic pumps P can be performed smoothly, regardless of whether the pump tubes C are deformed. The positions of the positioning pin (g) and the positioning hole (h) may be defined arbitrarily. Moreover, the present invention may be applied to a blood purification apparatus B including no positioning pin (g), with the attaching member 1 having no positioning hole (h).

The attaching member may have other additional functions or the like, as long as the attaching member includes a body attachable to a predetermined position of a blood purification apparatus, and a holding portion attached to the body and that holds a pump tube such that the pump tube is inclined in a direction in which the pump tube is attached to a peristaltic pump.

| REFERENCE SIGN LIST | |
|---|---|
| 1 | attaching member |
| 2 | body |
| 2a | inclined surface |
| 2b | central portion |
| 3 | holding portion |
| 3a | holding groove |
| 3b | anchoring hole (anchoring part) |
| K | fold (rocking axis) |
| A | anchor member |
| Aa | anchor hook |
| Ab | pushing portion |
| B | blood purification apparatus (monitoring apparatus) |
| Ba | predetermined position |
| C | pump tube |
| D | connector |
| M | monitor |
| P | peristaltic pump |
| S | stator |
| Sa | fitting recess |
| R | rotor |
| Ra | roller |
| a1, b1 | upper guide pin |
| a2, b2 | lower guide pin |
| L | rotating shaft |
| g | positioning pin |
| h | positioning hole |

The invention claimed is:

1. An attaching member to be attached to a blood purification apparatus including a peristaltic pump, the attaching member holding a pump tube to be squeezed in a predetermined direction by the peristaltic pump for liquid delivery, the attaching member comprising:
   a body attachable to a predetermined position of the blood purification apparatus; and
   a holding portion attached to the body and that holds the pump tube,
   wherein the holding portion holds the pump tube such that the pump tube is inclined, relative to the body, in a direction in which the pump tube is attached to the peristaltic pump, and
   wherein the holding portion holds a connector formed at both ends of the pump tube and the holding portion is connected to a flow route and the holding portion extends in an inclined state.

2. The attaching member according to claim 1, wherein the holding portion is displaceable when receiving a load generated at a time of attaching or detaching the pump tube to or from the peristaltic pump.

3. The attaching member according to claim 1, wherein the holding portion includes an anchoring part at which the holding portion is anchorable by an anchor member included in the blood purification apparatus; the pump tube is attachable to the peristaltic pump when the holding portion is anchored by the anchor member at the anchoring part; and the pump tube is detachable from the peristaltic pump by moving the anchor member when the anchor member is anchored to the holding portion at the anchoring part is moved.

4. A blood purification circuit connected to the pump tube according to claim 1, the blood purification circuit comprising a blood circuit through which blood is caused to extracorporeally circulate, and a flow route through which substitution fluid is introduced into the blood circuit or the flow route through which dialysate is introduced into a blood purifier connected to the blood circuit or drain liquid is discharged from the blood purifier.

5. The attaching member according to claim 1, wherein the direction in which the pump tube is attached to the peristaltic pump is a direction towards a bottom of a stator of the peristaltic pump.

6. The attaching member according to claim 1, wherein the direction in which the pump tube is attached to the peristaltic pump is a direction towards a bottom of a stator of the peristaltic pump, and when the body is attached to the blood purification apparatus, an angle of a bend of the pump tube is cancelled out or absorbed by an inclination of the pump tube.

7. An attaching member to be attached to a blood purification apparatus including a peristaltic pump, the attaching member holding a pump tube to be squeezed in a predetermined direction by the peristaltic pump for liquid delivery, the attaching member comprising:
a body attachable to a predetermined position of the blood purification apparatus; and
a holding portion attached to the body and that holds the pump tube,
wherein the holding portion holds the pump tube such that the pump tube is inclined, relative to the body, in a direction in which the pump tube is attached to the peristaltic pump, and
wherein the holding portion of the body is formed with a resin molded component that is form continuously, and the holding portion is attachable at an inclined state to the body by folding at folds extended along boundaries between the body and the holding portion.

8. The attaching member according to claim 7, wherein the holding portion holds a connector formed at both ends of the pump tube and connected to a flow route in an inclined state.

9. The attaching member according to claim 7, wherein the holding portion is displaceable when receiving a load generated at a time of attaching or detaching the pump tube to or from the peristaltic pump.

10. The attaching member according to claim 7, wherein the holding portion includes an anchoring part at which the holding portion is anchorable by an anchor member included in the blood purification apparatus; the pump tube is attachable to the peristaltic pump when the holding portion is anchored by the anchor member at the anchoring part; and the pump tube is detachable from the peristaltic pump by moving the anchor member when the anchor member is anchored to the holding portion at the anchoring part is moved.

11. A blood purification circuit connected to the pump tube according to claim 7, the blood purification circuit comprising a blood circuit through which blood is caused to extracorporeally circulate, and a flow route through which substitution fluid is introduced into the blood circuit or the flow route through which dialysate is introduced into a blood purifier connected to the blood circuit or drain liquid is discharged from the blood purifier.

12. The attaching member according to claim 7, wherein the direction in which the pump tube is attached to the peristaltic pump is a direction towards a bottom of a stator of the peristaltic pump.

13. The attaching member according to claim 7, wherein the direction in which the pump tube is attached to the peristaltic pump is a direction towards a bottom of a stator of the peristaltic pump, and when the body is attached to the blood purification apparatus, an angle of a bend of the pump tube is cancelled out or absorbed by an inclination of the pump tube.

14. An attaching member to be attached to a blood purification apparatus including a peristaltic pump, the attaching member holding a pump tube to be squeezed in a predetermined direction by the peristaltic pump for liquid delivery, the attaching member comprising:
a body attachable to a predetermined position of the blood purification apparatus; and
a holding portion attached to the body and that holds the pump tube,
wherein the holding portion holds the pump tube such that the pump tube is inclined in a direction in which the pump tube is attached to the peristaltic pump, and
wherein the body includes inclined surfaces that the holding portions attach to so that the pump tube is inclined in the direction in which the pump tube is attached to the peristaltic pump.

15. The attaching member according to claim 14, wherein the holding portion holds a connector formed at both ends of the pump tube and connected to a flow route in an inclined state.

16. The attaching member according to claim 14, wherein the inclined surfaces are inclined at an angle relative to a bottom surface of the body.

17. The attaching member according to claim 14, wherein the inclined surfaces are on opposing sides of the body with a central portion extending therebetween.

18. The attaching member according to claim 17, wherein the inclined surfaces extend away from the central portion towards a bottom surface of the body.

19. The attaching member according to claim 18, wherein the direction the pump tube is inclined is from the central portion towards the bottom surface of the body.

20. The attaching member according to claim 14, wherein the direction in which the pump tube is attached to the peristaltic pump is a direction towards a bottom of a stator of the peristaltic pump, and when the body is attached to the blood purification apparatus, an angle of a bend of the pump tube is cancelled out or absorbed by an inclination of the pump tube.

* * * * *